(12) United States Patent
Takahashi et al.

(10) Patent No.: US 12,324,731 B2
(45) Date of Patent: Jun. 10, 2025

(54) ABSORBENT ARTICLE

(71) Applicant: LIVEDO CORPORATION, Ehime (JP)

(72) Inventors: Yuki Takahashi, Tokushima (JP); Shingo Takeda, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 536 days.

(21) Appl. No.: 17/626,219

(22) PCT Filed: Jul. 6, 2020

(86) PCT No.: PCT/JP2020/026430
§ 371 (c)(1),
(2) Date: Jan. 11, 2022

(87) PCT Pub. No.: WO2021/010211
PCT Pub. Date: Jan. 21, 2021

(65) Prior Publication Data
US 2022/0313498 A1      Oct. 6, 2022

(30) Foreign Application Priority Data

Jul. 17, 2019   (JP) ................................ 2019-132057

(51) Int. Cl.
*A61F 13/475*      (2006.01)
(52) U.S. Cl.
CPC ............................ *A61F 13/4753* (2013.01)
(58) Field of Classification Search
CPC .............. A61F 13/4753; A61F 13/4942; A61F 2013/49088; A61F 2013/149092; A61F 2013/149093
See application file for complete search history.

(56) References Cited

U.S. PATENT DOCUMENTS 5,582,606 A * 12/1996 Bruemmer ............ A61F 13/511
604/385.28
6,440,117 B1    8/2002 Itoh et al.
(Continued)

FOREIGN PATENT DOCUMENTS

JP        6-209967        8/1994
JP       11-285510       10/1999
(Continued)

OTHER PUBLICATIONS

International Search Report issued Sep. 15, 2020 in International (PCT) Application No. PCT/JP2020/026430.

*Primary Examiner* — Nicholas J. Weiss
*Assistant Examiner* — Gabriella E Burnette
(74) *Attorney, Agent, or Firm* — Wenderoth, Lind & Ponack, L.L.P.

(57) ABSTRACT

An absorbent article (1) comprising a top sheet (2), a back sheet (3), an absorbent body (4) provided therebetween, and side sheets (5) provided on both sides of the top sheet (2) in a width direction, wherein; a leak-proof flap (6) is formed from a portion of the side sheet (5); the leak-proof flap (6) is configured such that a front end portion (6F) and a rear end portion (6B) are joined to the top sheet (2) at end fixing parts (8) and a middle portion (6M) stands up inward in the width direction; a flap elastic member (7) is provided on the leak-proof flap (6) so as to extend continuously from the front end portion (6F) to the rear end portion (6B), and the flap elastic member (7) is located inward in the width direction from the end fixing parts (8) at the front end portion (6F) and the rear end portion (6B).

11 Claims, 6 Drawing Sheets

(56) References Cited

U.S. PATENT DOCUMENTS

| | | | |
|---|---|---|---|
| 8,758,319 B2* | 6/2014 | Takahashi | A61F 13/4942 |
| | | | 604/385.28 |
| 11,471,339 B2* | 10/2022 | Ishikawa | A61F 13/4963 |
| 2002/0123733 A1 | 9/2002 | Itoh et al. | |
| 2004/0122410 A1 | 6/2004 | Itoh et al. | |
| 2011/0112500 A1 | 5/2011 | Wenzel et al. | |
| 2017/0000656 A1* | 1/2017 | Chatterjee | A61F 13/4902 |

FOREIGN PATENT DOCUMENTS

| | | | | |
|---|---|---|---|---|
| JP | 2012-501765 | | 1/2012 | |
| JP | 2012-125454 | | 7/2012 | |
| JP | 2015-2765 | | 1/2015 | |
| JP | 6518803 B1 * | | 5/2019 | A61F 13/475 |

* cited by examiner

[Fig. 1]
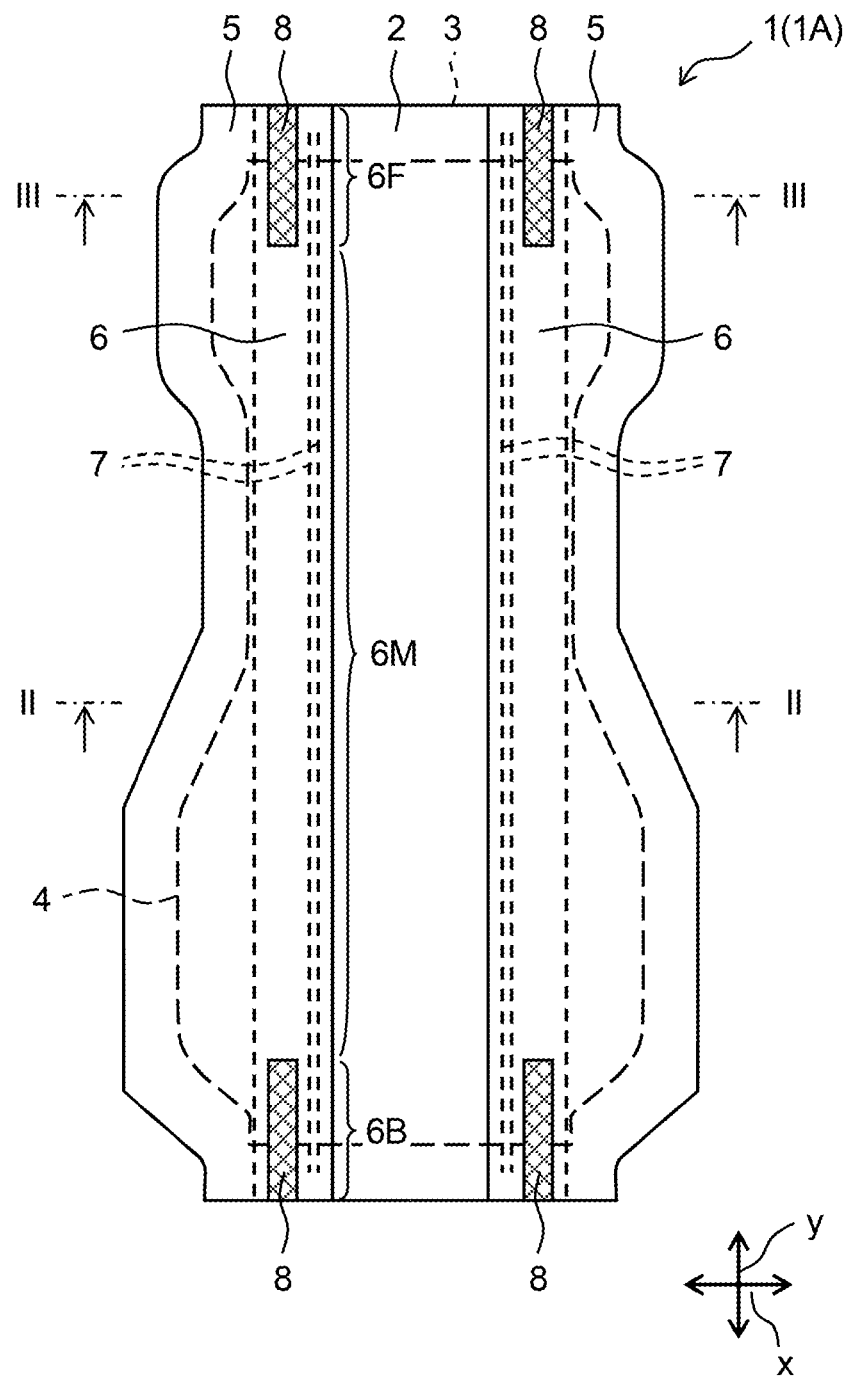

[Fig. 2]
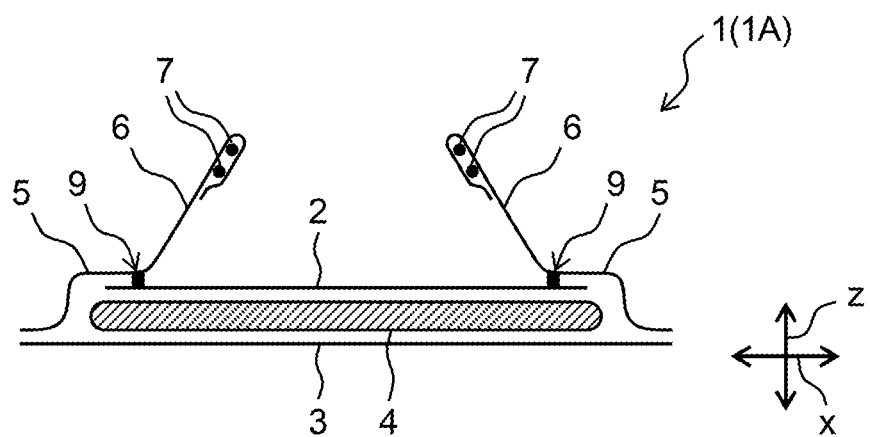
[Fig. 3]
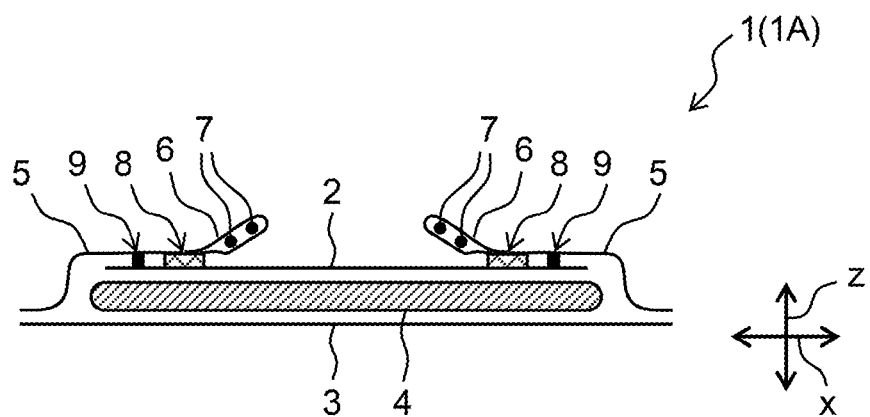

[Fig. 4]
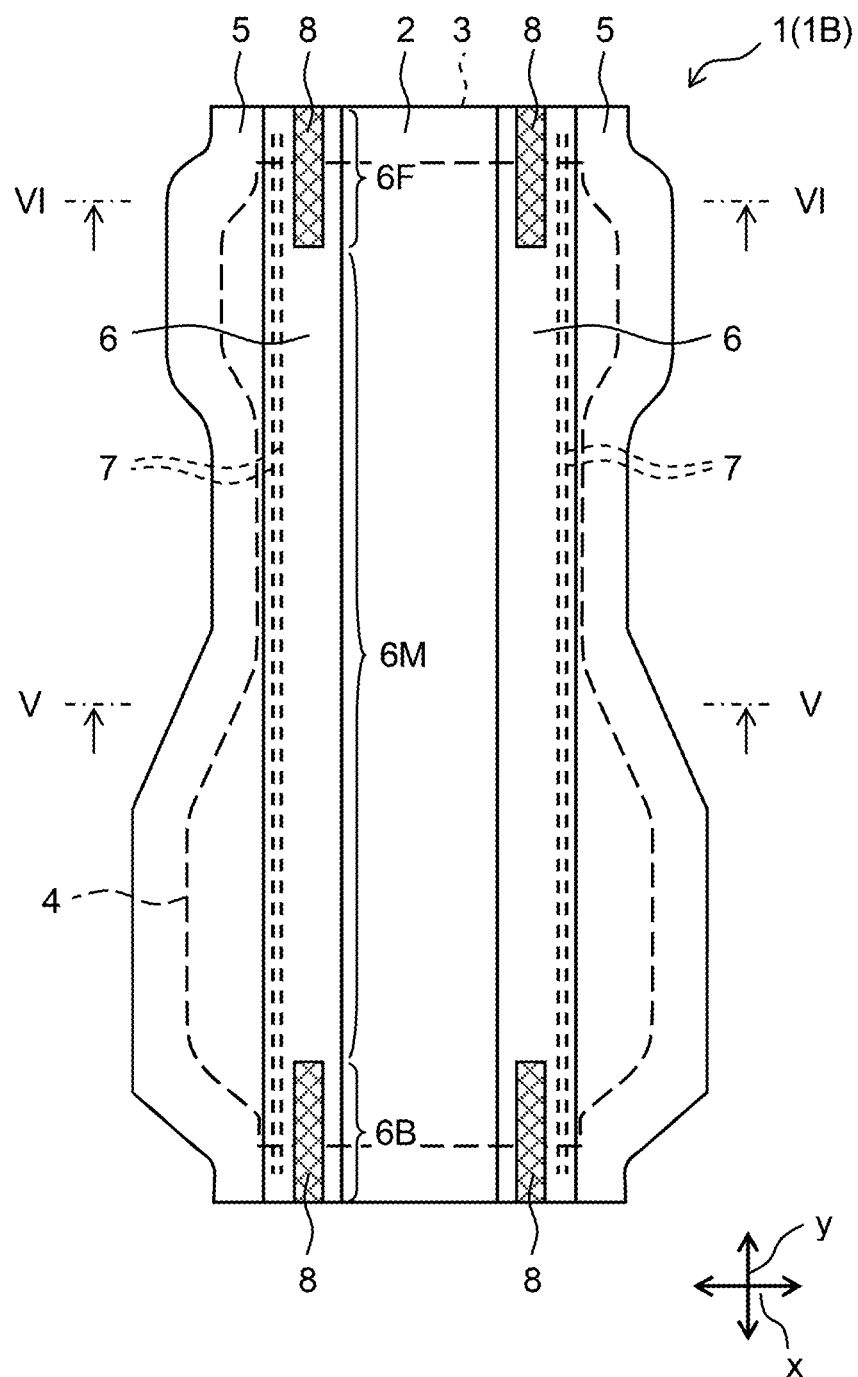

[Fig. 5]
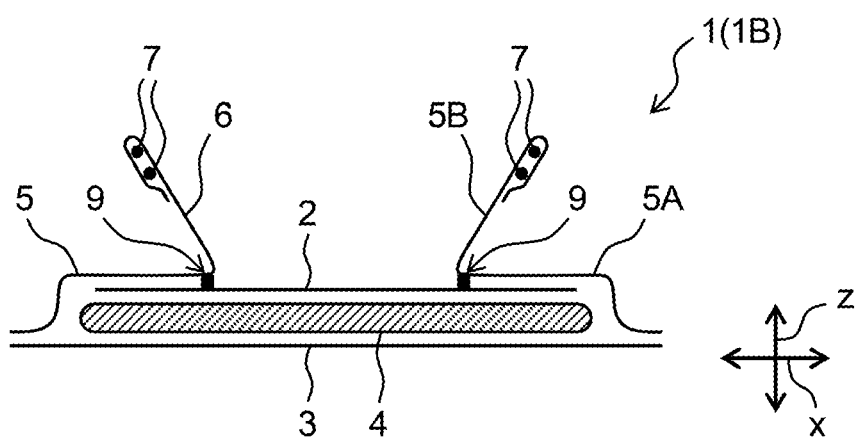
[Fig. 6]
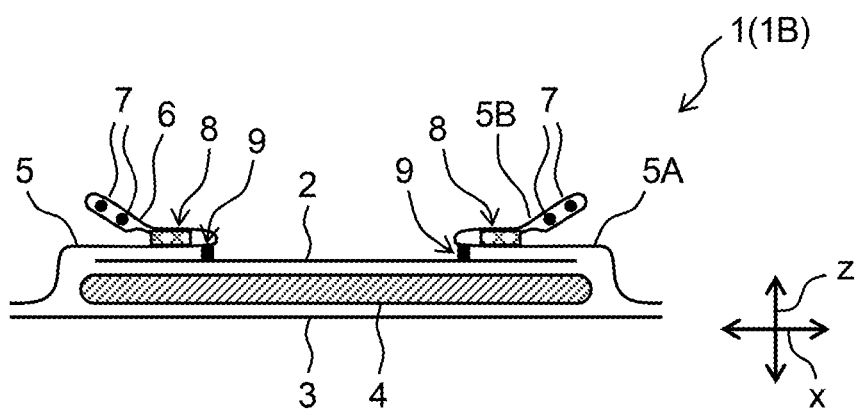

[Fig. 7]
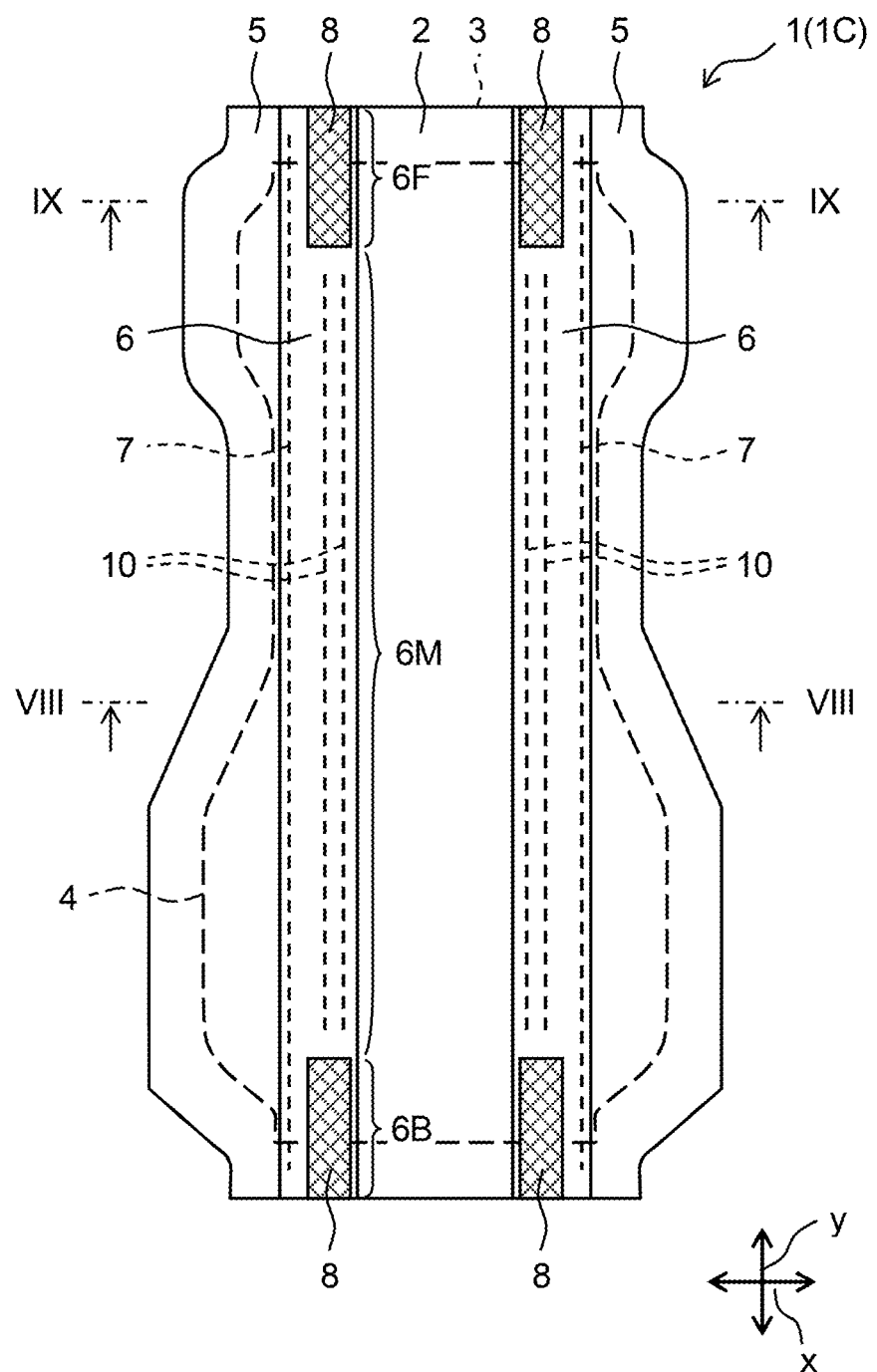

[Fig. 8]
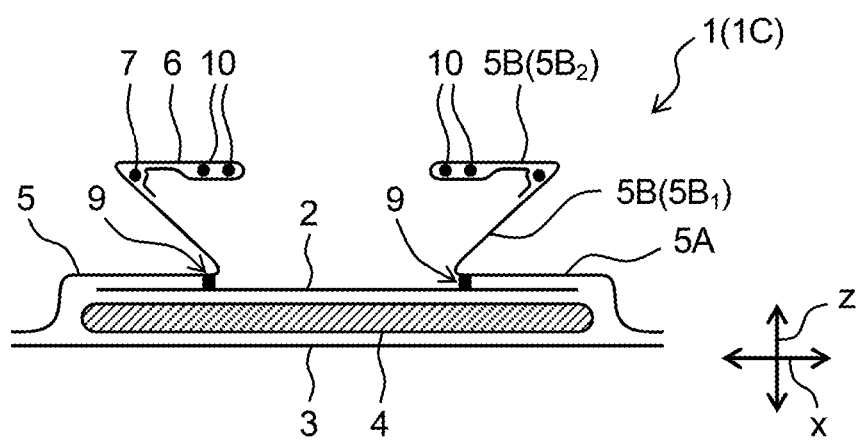
[Fig. 9]
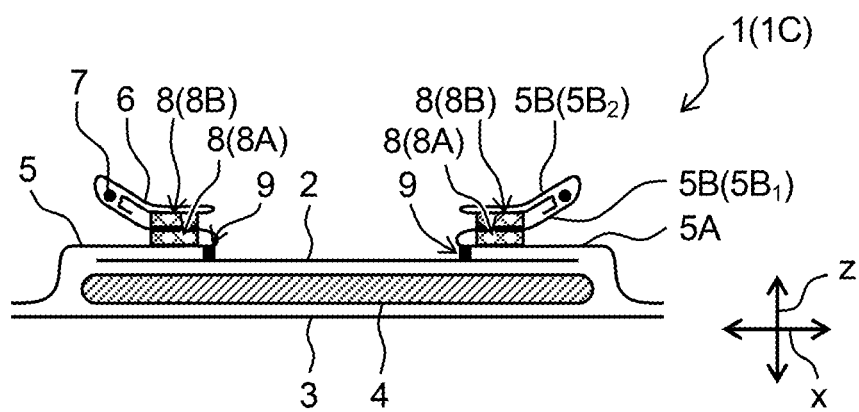

ABSORBENT ARTICLE

TECHNICAL FIELD

The present invention relates to an absorbent article such as a disposable diaper, an incontinence pad (including a light incontinence pad) and a sanitary napkin.

BACKGROUND ART

Conventionally, absorbent articles provided with a leak-proof flap on a skin facing side thereof are known. Various shapes of the leak-proof flap are known, as disclosed in Patent Literatures 1 and 2.

CITATION LIST

Patent Literature

Patent Literature 1
  Japanese Unexamined Laid-open Patent Application Publication No. H6-209967
Patent Literature 2
  Japanese Unexamined Laid-open Patent Application Publication No. H11-285510

SUMMARY OF INVENTION

Technical Problem

Absorbent articles can prevent lateral leakage of urine or the like excreted from a wearer by providing a leak-proof flap on a skin facing side thereof, but it is more preferable that it exhibits higher ability in preventing lateral leakage. The present invention has been achieved in view of the above circumstances, and an object of the present invention is to provide an absorbent article having excellent ability in preventing lateral leakage of urine or the like.

Solution to Problem

An absorbent article of the present invention which solves the above problems comprises a top sheet, a back sheet, an absorbent body provided therebetween, and side sheets provided on both sides of the top sheet in a width direction, wherein: a leak-proof flap is formed from a portion of the side sheet; the leak-proof flap is configured such that a front end portion and a rear end portion are joined to the top sheet at end fixing parts and a middle portion positioned between the front end portion and the rear end portion stands up inward in the width direction; a flap elastic member is provided on the leak-proof flap so as to extend continuously from the front end portion to the rear end portion; and the flap elastic member is located inward in the width direction from the end fixing parts at the front end portion and the rear end portion.

In the absorbent article of the present invention, since the leak-proof flap is configured as described above, the middle portion of the leak-proof flap in the front-rear direction stands up inward in the width direction, and the front end portion and the rear end portion are also able to stand up. Therefore, according to the absorbent article of the present invention, lateral leakage of urine or the like can be prevented in the middle portion of the leak-proof flap, as well as lateral leakage of urine or the like can be also prevented in the front end portion and the rear end portion.

In the above absorbent article, a plurality of the flap elastic members may be provided on the leak-proof flap, inward in the width direction from the end fixing part. When a plurality of the flap elastic members are provided in this manner, a free end, which is a tip of the standing leak-proof flap, is less likely to bite into a wearer's skin, and wearing feeling of the absorbent article can be improved.

The present invention also provides an absorbent article comprising a top sheet, a back sheet, an absorbent body provided therebetween, and side sheets provided on both sides of the top sheet in a width direction, wherein: a leak-proof flap is formed from a portion of the side sheet; the leak-proof flap is configured such that a front end portion and a rear end portion are joined to the side sheet at end fixing parts and a middle portion positioned between the front end portion and the rear end portion stands up outward in the width direction; a flap elastic member is provided on the leak-proof flap so as to extend continuously from the front end portion to the rear end portion; and the flap elastic member is located outward in the width direction from the end fixing parts at the front end portion and the rear end portion.

In the above absorbent article, the middle portion of the leak-proof flap in the front-rear direction stands up outward in the width direction, and the front end portion and the rear end portion are also able to stand up. Therefore, also in the absorbent article configured in the above manner, lateral leakage of urine or the like can be prevented in the middle portion of the leak-proof flap, as well as lateral leakage of urine or the like can be also prevented in the front end portion and the rear end portion.

In the above absorbent article, the side sheet may have a base part provided facing the top sheet and a folded part formed by folding back the side sheet at an inner edge of the base part in the width direction, and the leak-proof flap may be formed from the folded part, and the front end portion and the rear end portion of the folded part may be joined to the base part at the end fixing parts. The side sheet may have a base part provided facing the top sheet, a first folded part formed by folding back the side sheet at an inner edge of the base part in the width direction, and a second folded part formed by folding back the side sheet at an outer edge of the first folded part in the width direction; the leak-proof flap may be formed from the first folded part and the second folded part, the front end portion and the rear end portion of the first folded part may be joined to the base part at first end fixing parts, and the front end portion and the rear end portion of the second folded part may be joined to the first folded part at second end fixing parts; the flap elastic member may be provided at the first folded part and/or the second folded part so as to extend continuously from the front end portion to the rear end portion, and the flap elastic member may be located outward in the width direction from the first end fixing parts at the front end portion and the rear end portion. In the case where the leak-proof flap is configured as in the latter manner, it is preferable that a second flap elastic member is provided at the middle portion of the second folded part, inward in the width direction from an outer end of the first end fixing part in the width direction. Thereby, the middle portion of the second folded part can easily stand up so as to come into contact with a wearer's skin in a planar manner, and wearing feeling of the absorbent article is improved.

In the above absorbent article, a plurality of the flap elastic members may be provided on the leak-proof flap, outward in the width direction from the end fixing part. When a plurality of the flap elastic members are provided in this manner, a free end, which is a tip of the standing leak-proof flap, is less likely to bite into a wearer's skin, and wearing feeling of the absorbent article can be improved.

It is preferable that the flap elastic member is attached to the leak-proof flap with an adhesive applied to the flap elastic member. When the flap elastic member is attached to the leak-proof flap in this manner, an application area of the adhesive in the leak-proof flap can be reduced. Therefore, the leak-proof flap can be formed soft, thereby improving contact with a wearer's skin.

Advantageous Effects of Invention

In the absorbent article of the present invention, the middle portion of the leak-proof flap in the front-rear direction stands up inward or outward in the width direction, and the front end portion and the rear end portion are also able to stand up. Therefore, according to the absorbent article of the present invention, lateral leakage of urine or the like can be prevented in the middle portion of the leak-proof flap, as well as lateral leakage of urine or the like can be also prevented in the front end portion and the rear end portion.

BRIEF DESCRIPTION OF THE DRAWINGS

FIG. 1 shows a plan view of an incontinence pad, as an example of the absorbent article of the present invention, seen from a top sheet side.

FIG. 2 shows a cross-sectional view along a line II-II of the absorbent article shown in FIG. 1.

FIG. 3 shows a cross-sectional view along a line III-III of the absorbent article shown in FIG. 1.

FIG. 4 shows a plan view of an incontinence pad, as another example of the absorbent article of the present invention, seen from a top sheet side.

FIG. 5 shows a cross-sectional view along a line V-V of the absorbent article shown in FIG. 4.

FIG. 6 shows a cross-sectional view along a line VI-VI of the absorbent article shown in FIG. 4.

FIG. 7 shows a plan view of an incontinence pad, as another example of the absorbent article of the present invention, seen from a top sheet side.

FIG. 8 shows a cross-sectional view along a line VIII-VIII of the absorbent article shown in FIG. 7.

FIG. 9 shows a cross-sectional view along a line IX-IX of the absorbent article shown in FIG. 7.

DESCRIPTION OF THE PREFERRED EMBODIMENTS

An absorbent article of the present invention is provided with a leak-proof flap on a skin facing side thereof. The leak-proof flap is provided with a flap elastic member and its front end portion and rear end portion are fixed on the skin facing side of the absorbent article, and thereby, a middle portion between the front end portion and the rear end portion is formed so as to stand up. The flap elastic member is disposed on the leak-proof flap so as to extend continuously from the front end portion to the rear end portion, whereby not only the middle portion but also the front end portion and the rear end portion are formed so as to be able to stand up. In the absorbent article of the present invention, since the leak-proof flap is configured in such a manner, lateral leakage of urine or the like can be prevented in the middle portion of the leak-proof flap, as well as the effect of preventing lateral leakage of urine or the like can be enhanced in the front end portion and the rear end portion.

Hereinafter, the absorbent article of the present invention is explained with reference to the drawings. In the drawings, an incontinence pad is taken as an example of the absorbent article, and configuration examples of the absorbent article provided with a leak-proof flap of various embodiments is shown. However, the present invention is not limited to the embodiments shown in the drawings.

FIGS. 1 to 3 show an example of the absorbent article provided with a leak-proof flap according to a first embodiment. FIG. 1 shows a plan view of an absorbent article (an incontinence pad) seen from a top sheet side, FIG. 2 shows a cross-sectional view along a line II-II of the absorbent article shown in FIG. 1, and FIG. 3 shows a cross-sectional view along a line III-III of the absorbent article shown in FIG. 1. In the drawings of the present application, the arrow x represents a width direction, the arrow y represents a front-rear direction, and a direction perpendicular to a plane formed by the arrows x and y represents a thickness direction z. In FIG. 1, an upper side of the drawing corresponds to a front side of the absorbent article, and a lower side of the drawing corresponds to a rear side of the absorbent article.

An absorbent article 1 (1A) comprises a top sheet 2, a back sheet 3 and an absorbent body 4 provided between them. The top sheet 2 is disposed on a skin facing side of the absorbent body 4, and the back sheet 3 is disposed on a non-skin facing side of the absorbent body 4. Excrement which has passed through the top sheet 2 is stored by the absorbent body 4. The back sheet 3 prevents excrement from leaking out.

The absorbent article 1 has a front-rear direction y and a width direction x. The front-rear direction y means a direction extending in a front-rear direction at a crotch of a wearer when the absorbent article is worn. The width direction x means a direction orthogonal to the front-rear direction y on the same plane as the absorbent article, and corresponds to a left-right direction of a wearer when the absorbent article is worn. In addition, a skin facing side is a side facing a wearer's skin and a non-skin facing side is an opposite side of that when the wearer wears the absorbent article.

The top sheet 2 is a sheet which is disposed on the skin facing side of the absorbent body 4 and is provided so as to face a wearer's skin in wearing the absorbent article. The top sheet 2 is preferably liquid-permeable. As the top sheet 2, a nonwoven fabric made from hydrophilic fibers such as cellulose, rayon and cotton; a nonwoven fabric which is formed from hydrophobic fibers such as polyolefin (e.g., polypropylene and polyethylene), polyester (e.g., PET) and polyamide (e.g., nylon), and in which the hydrophobic fibers are hydrophilized with a surfactant on the surface thereof; or the like can be used, for example. As the top sheet 2, a woven fabric, a knitted fabric, a plastic film having holes may be also used.

The back sheet 3 is a sheet which is disposed on the non-skin facing side of the absorbent body 4 and is preferably liquid-impermeable. As the back sheet 3, a nonwoven fabric made from hydrophobic fibers such as polyolefin (e.g., polypropylene and polyethylene), polyester (e.g., PET) and polyamide (e.g., nylon); a plastic film; or the like can be used. As the back sheet 3, a laminate of a nonwoven fabric and a plastic film may be also used.

In the case where a nonwoven fabric is used for the top sheet 2 or the back sheet 3, a spunbonded nonwoven fabric, an air-through nonwoven fabric, a point-bonded nonwoven fabric, a meltblown nonwoven fabric, an airlaid nonwoven fabric, an SMS nonwoven fabric or the like is preferably used as the nonwoven fabric.

The absorbent body 4 is not particularly limited as long as it contains an absorbent material that is capable of absorbing excrement such as urine. As the absorbent body 4, a shaped product of an absorbent material, which is formed into a certain shape, may be used, or the shaped product wrapped with a cover sheet such as a paper (e.g., a tissue paper and a thin paper) or a liquid-permeable nonwoven fabric may be used, for example. Examples of the absorbent material include, for example, a hydrophilic fiber such as a pulp fiber, and an absorbent polymer such as a polyacrylic absorbent polymer, a polyasparaginic absorbent polymer, a cellulosic absorbent polymer and a starch-acrylonitrile absorbent polymer. The absorbent material may include a thermal fusion fiber such as a polyolefin (e.g., polyethylene and polypropylene) fiber, a polyester (e.g., PET) fiber and a polyamide fiber. These thermal fusion fibers may be hydrophilized with a surfactant or the like for increasing affinity with urine or the like.

The absorbent material preferably includes a hydrophilic fiber in view of increasing absorption speed of urine or the like. In addition, in view of enhancing absorption capacity, the absorbent material preferably includes an absorbent polymer. Therefore, the absorbent body 4 preferably contains both a hydrophilic fiber (especially a pulp fiber) and an absorbent polymer. In this case, the absorbent material formed by mixing an absorbent polymer with a hydrophilic fiber assembly, or dispersing an absorbent polymer on a hydrophilic fiber assembly is preferably used, for example.

The absorbent body 4 may be a sheet-like absorbent body. Examples of the sheet-like absorbent body include those that are configured so as to contain an absorbent polymer but not contain a pulp fiber between nonwoven fabrics. Thus formed sheet-like absorbent body enables having high absorption capacity since it contains an absorbent polymer between nonwoven fabrics. In addition, since the sheet-like absorbent body does not contain a pulp fiber between nonwoven fabrics, it can be formed thin without being bulky.

For the sheet-shaped absorbent body, an absorbent fiber may be used as the absorbent material. Also in this case, the sheet-like absorbent body is formed thin without being bulky. Examples of the absorbent fiber include a fiber having a protonated carboxyl group or a carboxylate group. The absorbent fiber can be prepared by, for example, hydrolyzing an acrylic fiber, thereby converting a nitrile group contained in the acrylic fiber to a carboxylic group. The carboxyl group contained in the absorbent fiber preferably forms an alkaline metal salt or an ammonium salt. The absorbent fiber can be also prepared by immersing a hydrophilic fiber in acrylic acid to deposit acrylic acid on the surface of the fiber.

A shape (planar shape) of the absorbent body 4 is not particularly limited. Examples of the shape of the absorbent body 4 include a substantially rectangular shape, an hourglass shape, a gourd shape, a battledore shape, and others.

Side sheets 5 are provided on both sides of the top sheet 2 in the width direction x, and a leak-proof flap 6 is formed from a portion of the side sheet 5. The side sheet 5 is joined to both sides of the top sheet 2 in the width direction x, an outer portion of the side sheet 5 in the width direction x is stacked on the top sheet 2 and/or the back sheet 3, and an inner portion of the side sheet 5 in the width direction x forms the leak-proof flap 6. The side sheet 5 is preferably liquid-impermeable and can be made of a sheet material that can be used for the back sheet 3. The side sheet 5 is preferably made of, for example, a liquid-impermeable plastic film, a liquid-impermeable nonwoven fabric, or the like.

The leak-proof flap 6 has a front end portion 6F, a rear end portion 6B and a middle portion 6M between them in the front-rear direction y, and the front end portion 6F and the rear end portion 6B are fixed on a skin facing side of the absorbent article at end fixing parts 8. In the leak-proof flap 6, the front end portion 6F means a portion in the range from a rear end of the end fixing part 8 provided on the front end portion 6F to a front end of the leak-proof flap 6 in the front-rear direction y, and the rear end of the end fixing part 8 provided on the front end portion 6F comes to be a boundary between the front end portion 6F and the middle portion 6M. The rear end portion 6B means a portion in the range from a front end of the end fixing part 8 provided on the rear end portion 6B to a rear end of the leak-proof flap 6, and the front end of the end fixing part 8 comes to be a boundary between the rear end portion 6B and the middle portion 6M. The lengths of the front end portion 6F and the rear end portion 6B of the leak-proof flap 6 in the front-rear direction y are preferably 3% or more, more preferably 5% or more, and preferably 20% or less, more preferably 15% or less of the length of the leak-proof flap 6 in the front-rear direction y, respectively. For the side sheet 5, a front end portion, a rear end portion and a middle portion are defined according to the partition of the leak-proof flap 6 in the front-rear direction y.

In the absorbent article 1A, as shown in FIG. 2, provided that an inner edge, with respect to the width direction x, of a joint part 9 with the top sheet 2 in the middle portion of the side sheet 5 is set as a boundary, a portion located on an inner side in the width direction x of the boundary (specifically, an inner portion in the width direction x including the front end portion, the rear end portion and the middle portion) serves as the leak-proof flap 6. The leak-proof flap 6 is formed so that the middle portion 6M stands up from the joint part 9 where the side sheet 5 is joined to the top sheet 2. The front end portion 6F and the rear end portion 6B of the leak-proof flap 6 are fixed on the skin facing side of the absorbent article at the end fixing parts 8, whereby standing of the front end portion 6F and the rear end portion 6B is suppressed as compared with the middle portion 6M (refer to FIGS. 1 and 3). A portion located on an outer side in the width direction x of the joint part 9 with the top sheet 2 in the middle portion of the side sheet 5 (specifically, an outer portion in the width direction x including the front end portion, the rear end portion and the middle portion) is provided facing to the top sheet 2 as a base part, and may be provided further facing to the back sheet 3. The base part of the side sheet 5 is joined to the top sheet 2 (or further the back sheet 3), and is formed so as not to stand up from the top sheet 2.

In the absorbent article 1A, the front end portion 6F and the rear end portion 6B of the leak-proof flap 6 are joined to the top sheet 2 at the end fixing parts 8, and a flap elastic member 7 extending in the front-rear direction y is provided on the leak-proof flap 6. Thereby, the middle portion 6M of the leak-proof flap 6 stands up inward in the width direction x. By raising the middle portion 6M of the leak-proof flap 6, lateral leakage of urine or the like can be prevented in a crotch part.

The end fixing part 8 is located at an inner position in the width direction x than the joint part 9 where the side sheet 5 is joined to the top sheet 2 in the middle portion of the side sheet 5. The end fixing part 8 is formed by a known joining means such as an adhesive, heat welding, or ultrasonic welding. The end fixing part 8 is formed only in a part in the width direction x of the front end portion 6F and in a part in the width direction x of the rear end portion 6B in the leak-proof flap 6, and in the absorbent article 1A, the end fixing part 8 is not formed within a certain range from an inner edge of the leak-proof flap 6 in the width direction x. At the front end portion 6F and the rear end portion 6B of the leak-proof flap 6, the end fixing part 8 is not formed in a region, for example, preferably within 10%, more preferably within 20%, even more preferably within 25% of the length of the leak-proof flap 6 in the width direction x from the inner edge of the leak-proof flap 6 in the width direction x. That is, the end fixing part 8 is preferably located at a distance of 10% or more, more preferably 20% or more, even more preferably 25% or more of the length of the leak-proof flap 6 in the width direction x from the inner edge of the leak-proof flap 6 in the width direction x. Meanwhile, in view of promoting standing of the middle portion 6M of the leak-proof flap 6, the end fixing part 8 is preferably formed in a region within 60%, more preferably within 50% of the length of the leak-proof flap 6 in the width direction x from the inner edge of the leak-proof flap 6 in the width direction x.

In the absorbent article 1A, the flap elastic member 7 is provided at the middle portion 6M of the leak-proof flap 6, and is further provided at the front end portion 6F and the rear end portion 6B. Specifically, the flap elastic member 7 is provided so as to extend continuously from the front end portion 6F to the rear end portion 6B in the leak-proof flap 6, and is located inward in the width direction x from the end fixing part 8 at the front end portion 6F and the rear end portion 6B. By providing the flap elastic member 7 in this manner, the leak-proof flap 6 can stand up also at the front end portion 6F and the rear end portion 6B, and lateral leakage of urine or the like can be prevented in abdomen or back of a wearer. Moreover, since standing height of the front end portion 6F and the rear end portion 6B of the leak-proof flap 6 is suppressed by the end fixing part 8 as compared with the middle portion 6M, a wearer is less likely to feel discomfort even when the leak-proof flap 6 stands up on abdomen or back of a wearer.

The flap elastic member 7 is preferably located 1 mm or more, more preferably 2 mm or more inward in the width direction x from the end fixing part 8. This allows the leak-proof flap 6 to enhance leak-proof ability at the front end portion 6F and the rear end portion 6B. Meanwhile, in view of ensuring the length of the end fixing part 8 in the width direction x, the flap elastic member 7 is preferably located 20 mm or less, more preferably 15 mm or less inward in the width direction x from the end fixing part 8. In the case where a plurality of the flap elastic members 7 are provided, at least one flap elastic member 7 is preferably disposed as such.

A front end of the flap elastic member 7 is located forward of a rear end of the front end portion 6F of the leak-proof flap 6, and a rear end of the flap elastic member 7 is located rearward of a front end of the rear end portion 6B of the leak-proof flap 6. The front end of the flap elastic member 7 is preferably located forward of a center of the front end portion 6F of the leak-proof flap 6 in the front-rear direction y, and the rear end of the flap elastic member 7 is preferably located rearward of a center of the rear end portion 6B of the leak-proof flap 6 in the front-rear direction y. Thereby, the effect of preventing lateral leakage at the front end portion 6F and the rear end portion 6B of the leak-proof flap 6 can be enhanced. It is also preferable that the flap elastic member 7 extends forward of a front end of the absorbent body 4 and rearward of a rear end of the absorbent body 4.

In the absorbent article 1A, a plurality of the flap elastic members 7 may be provided inward in the width direction x from the end fixing part 8. When a plurality of the flap elastic members 7 are provided in this manner, a free end, which is a tip of the standing leak-proof flap 6, is less likely to bite into a wearer's skin, and wearing feeling of the absorbent article can be improved.

In the absorbent article 1A, it is preferable that the leak-proof flap 6 is not provided with such elastic member that extends forward of a rear end of the end fixing part 8 of the front end portion 6F, located outward in the width direction x from an inner end of the end fixing part 8 of the front end portion 6F in the width direction x, or such elastic member that extends rearward of a front end of the end fixing part 8 of the rear end portion 6B, located outward in the width direction x from an inner end of the end fixing part 8 of the rear end portion 6B in the width direction x. When the leak-proof flap 6 is not provided with such an elastic member, inner portions in the width direction x of the front end portion 6F and the rear end portion 6B of the leak-proof flap 6 can easily stand up.

Next, other configuration examples of the absorbent article of the present invention are explained with reference to FIGS. 4 to 9. FIGS. 4 to 6 show an example of the absorbent article provided with a leak-proof flap according to a second embodiment, and FIGS. 7 to 9 show an example of the absorbent article provided with a leak-proof flap according to a third embodiment. FIG. 4 shows a plan view of an absorbent article (an incontinence pad) seen from a top sheet side, FIG. 5 shows a cross-sectional view along a line V-V of the absorbent article shown in FIG. 4, and FIG. 6 shows a cross-sectional view along a line VI-VI of the absorbent article shown in FIG. 4. FIG. 7 shows a plan view of an absorbent article (an incontinence pad) seen from a top sheet side, FIG. 8 shows a cross-sectional view along a line VIII-VIII of the absorbent article shown in FIG. 7, and FIG. 9 shows a cross-sectional view along a line IX-IX of the absorbent article shown in FIG. 7. In the absorbent articles shown in FIGS. 4 to 9, the same components as those in FIGS. 1 to 3 are indicated by the same reference numerals, and the details of these components are referred to the above description.

An absorbent article 1 (1B, 1C) comprises a top sheet 2, a back sheet 3 and an absorbent body 4 provided between them, and side sheets 5 are provided on both sides of the top sheet 2 in the width direction x. A leak-proof flap 6 is formed from a portion of the side sheet 5.

In the absorbent article 1B and the absorbent article 1C, a front end portion 6F and a rear end portion 6B of the leak-proof flap 6 are joined to the side sheet 5 at end fixing parts 8, and a flap elastic member 7 extending in the front-rear direction y is provided on the leak-proof flap 6. Thereby, the middle portion 6M of the leak-proof flap 6 stands up outward in the width direction x. In detail, the side sheet 5 has a base part 5A provided facing the top sheet 2 and a folded part 5B formed by folding back the side sheet 5 at an inner edge of the base part 5A, and the leak-proof flap 6 is formed from the folded part 5B. The front end portion 6F and the rear end portion 6B of the folded part 5B are joined to the base part 5A at the end fixing parts 8, and as a result, the middle portion 6M of the folded part 5B stands up outward in the width direction x. Thereby, lateral leakage of urine or the like can be prevented in a crotch part.

In the absorbent article 1B and the absorbent article 1C, the flap elastic member 7 is provided at the folded part 5B of the side sheet 5, which forms the leak-proof flap 6, so as to extend continuously from the front end portion 6F to the rear end portion 6B, and the flap elastic member 7 is located outward in the width direction x from the end fixing part 8 at the end portion 6F and the rear end portion 6B. By providing the flap elastic member 7 in this manner, the leak-proof flap 6 can stand up also at the front end portion 6F and the rear end portion 6B, and lateral leakage of urine or the like can be prevented in abdomen or back of a wearer. Moreover, since standing height of the front end portion 6F and the rear end portion 6B of the leak-proof flap 6 is suppressed by the end fixing part 8 as compared with the middle portion 6M, a wearer is less likely to feel discomfort even when the leak-proof flap 6 stands up on abdomen or back of a wearer. In particular, in the absorbent article 1B and the absorbent article 1C, since the front end portion 6F and the rear end portion 6B of the leak-proof flap 6 can stand up outward in the width direction x, the leak-proof flap 6 is likely to come into contact with a skin of a wearer's abdomen or back in a planar manner, and a wearer is further less likely to feel discomfort in abdomen or back of a wearer.

The flap elastic member 7 is preferably located 1 mm or more, more preferably 2 mm or more outward in the width direction x from the end fixing part 8. This allows the leak-proof flap 6 to enhance leak-proof ability at the front end portion 6F and the rear end portion 6B. Meanwhile, in view of ensuring the length of the end fixing part 8 in the width direction x, the flap elastic member 7 is preferably located 20 mm or less, more preferably 15 mm or less outward in the width direction x from the end fixing part 8. In the case where a plurality of the flap elastic members 7 are provided, at least one flap elastic member 7 is preferably disposed as such.

In the absorbent article 1B and the absorbent article 1C, a plurality of the flap elastic members 7 may be provided outward in the width direction x from the end fixing part 8. When a plurality of the flap elastic members 7 are provided in this manner, a free end, which is a tip of the standing leak-proof flap 6, is less likely to bite into a wearer's skin, and wearing feeling of the absorbent article can be improved.

In the absorbent article 1B and the absorbent article 1C, the end fixing part 8 is located at an outer position in the width direction x than the joint part 9 where the base part 5A of the side sheet 5 is joined to the top sheet 2. The end fixing part 8 is formed by a known joining means such as an adhesive, heat welding, or ultrasonic welding. The end fixing part 8 is formed only in a part in the width direction x of the front end portion 6F and in a part in the width direction x of the rear end portion 6B in the leak-proof flap 6, and the end fixing part 8 is not formed within a certain range from an outer edge of the leak-proof flap 6 in the width direction x. At the front end portion 6F and the rear end portion 6B of the leak-proof flap 6, the end fixing part 8 is not formed in a region, for example, preferably within 10%, more preferably within 20%, even more preferably within 25% of the length of the leak-proof flap 6 in the width direction x from the outer edge of the leak-proof flap 6 in the width direction x. That is, the end fixing part 8 is preferably located at a distance of 10% or more, more preferably 20% or more, even more preferably 25% or more of the length of the leak-proof flap 6 in the width direction x from the outer edge of the leak-proof flap 6 in the width direction x. Meanwhile, in view of promoting the standing of the middle portion 6M of the leak-proof flap 6, the end fixing part 8 is preferably formed in a region within 60%, more preferably within 50% of the length of the leak-proof flap 6 in the width direction x from the outer edge of the leak-proof flap 6 in the width direction x.

The inner edge of the base part 5A of the side sheet 5 in the width direction x is preferably joined to the top sheet 2, and more preferably joined to the top sheet 2 in the entire front-rear direction y. Thereby, the folded part 5B of the side sheet 5 stands up from the inner edge of the base part 5A of the side sheet 5, thereby easily forming the leak-proof flap 6 properly.

In the case where the leak-proof flap 6 is formed so as to stand up outward in the width direction x, the leak-proof flap 6 may be formed such that the side sheet 5 is folded into a lying V-shape in the cross section of the width direction x, as in the absorbent article 1B, and may be formed such that the side sheet 5 is folded into a Z-shape in the cross section of the width direction x, as in the absorbent article 1C. In either case, the leak-proof flap 6 is formed so as to stand up outward in the width direction x from the top sheet 2, and by forming the leak-proof flap 6 in this manner, urine or the like excreted from a wearer can be received in a wider range in the width direction x.

In the absorbent article 1B, the leak-proof flap 6 is formed so as to stand up straight outward in the width direction x. That is, the leak-proof flap 6 is formed so as to stand up straight outward in the width direction x without being folded between a standing base part which is a starting point of standing and a free end which is a tip of standing. When the leak-proof flap 6 is formed in this manner, the leak-proof flap 6 is formed in a bowl shape in the cross section in the width direction x, and urine or the like excreted from a wearer is suitably easily received. In addition, the leak-proof flap 6 is likely to come into contact with a wearer's crotch in a planar manner, and wearing feeling of the absorbent article is improved.

In the absorbent article 1C, the leak-proof flap 6 is formed by being folded inward in the width direction x between a standing base part which is a starting point of standing and a free end which is a tip of standing. That is, the folded part 5B of the side sheet 5 includes a first folded part $5B_1$ that stands up outward in the width direction x and a second folded part $5B_2$ that is folded back at an outer edge of the first folded part $5B_1$ in the width direction x, and the leak-proof flap 6 is formed from the first folded part $5B_1$ and the second folded part $5B_2$. The first folded part $5B_1$ is formed by folding back the side sheet 5 at the inner edge of the base part 5A in the width direction x.

In the absorbent article 1C, the front end portion 6F and the rear end portion 6B of the first folded part $5B_1$ are joined to the base part 5A of the side sheet 5 at the end fixing parts 8, whereby the middle portion 6M of the first folded part $5B_1$ can stand up outward in the width direction x. In the absorbent article 1C, the end fixing part 8 in which the first folded part $5B_1$ is joined to the side sheet 5 is referred to as a "first end fixing part" and is denoted with a reference numeral "8A". Further, in the absorbent article 1C, it is preferable that the front end portion 6F and the rear end portion 6B of the second folded part $5B_2$ are joined to the first folded part $5B_1$ at second end fixing parts 8B, whereby the middle portion 6M of the second folded part $5B_2$ can easily stand up so as to come into contact with a wearer's skin in a planar manner, and wearing feeling of the absorbent article is improved.

In the absorbent article 1C, the flap elastic member 7 may be provided at the first folded part $5B_1$ or the second folded part $5B_2$, may be provided at both the first folded part $5B_1$ and the second folded part $5B_2$, or may be provided at a boundary between the first folded part $5B_1$ and the second folded part $5B_2$. In either case, the flap elastic member 7 is provided so as to extend continuously from the front end portion 6F to the rear end portion 6B in the leak-proof flap 6, and the flap elastic member 7 is located outward in the width direction x from the first end fixing parts 8A at the front end portion 6F and the rear end portion 6B. By providing the flap elastic member 7 in this manner, the front end portion 6F and the rear end portion 6B of the leak-proof flap 6 are likely to come into contact with a skin of a wearer's abdomen or back in a planar manner when they stand up, and a wearer is less likely to feel discomfort in a wearer's abdomen or back.

In the absorbent article 1C, it is preferable that a second flap elastic member 10 is provided at the middle portion 6M of the second folded part $5B_2$, inward in the width direction x from an outer end of the first end fixing part 8A in the width direction x. In this case, the flap elastic member with the reference numeral "7" described above can be referred to as a "first flap elastic member". When the second flap elastic member 10 is provided at the middle portion 6M of the second folded part $5B_2$, the second folded part $5B_2$ of the leak-proof flap 6 is likely to stand up toward a wearer's skin in a planar manner, and wearing feeling of the absorbent article is improved. Only one second flap elastic member 10 may be provided, or a plurality of second flap elastic members 10 may be provided side by side in the width direction x. The second flap elastic member 10 is preferably provided so as not to overlap with the end fixing part 8.

In the absorbent article 1B and the absorbent article 1C, it is preferable that the leak-proof flap 6 is not provided with such elastic member that extends forward of a rear end of the end fixing part 8 of the front end portion 6F and is located inward in the width direction x from an outer end of the end fixing part 8 of the front end portion 6F in the width direction x, or such elastic member that extends rearward of a front end of the end fixing part 8 of the rear end portion 6B and is located inward in the width direction x from an outer end of the end fixing part 8 of the rear end portion 6B in the width direction x. When the leak-proof flap 6 is not provided with such an elastic member, outer portions in the width direction x of the front end portion 6F and the rear end portion 6B of the leak-proof flap 6 can easily stand up.

As the flap elastic member 7 and the second flap elastic member 10, elastic stretchable materials such as a polyurethane thread, a polyurethane film, a natural rubber and the like, that are generally used for absorbent articles, can be used. The elastic member is preferably fixed with an adhesive such as a hot melt adhesive in a stretched state. For example, a polyurethane thread having a fineness of 40 dtex to 1,240 dtex is stretched at a ratio of 1.1 to 5.0 times and is disposed to be fixed. As the adhesive, a rubber hot-melt adhesive is preferably used. Regarding the above-described ratio, an unexpanded state is defined as 1.0 time.

The flap elastic member 7 is preferably attached to the leak-proof flap 6 with an adhesive applied to the flap elastic member 7. When the flap elastic member 7 is attached to the leak-proof flap 6 in this manner, an application area of the adhesive in the leak-proof flap 6 can be reduced. Therefore, the leak-proof flap 6 can be formed soft, thereby improving contact with a wearer's skin. Similarly, the second flap elastic member 10 is preferably attached to the leak-proof flap 6 with an adhesive applied to the second flap elastic member 10. The application area of the adhesive in the leak-proof flap 6 is preferably 50% or less, more preferably 30% or less of an area of the leak-proof flap 6.

In the above, the absorbent article of the present invention is explained with reference to the drawings; however, the absorbent article of the present invention is not limited to the incontinence pad as shown in the drawings, and may be a disposable diaper, a light incontinence pad or a sanitary napkin.

In the case that the absorbent article is a disposable diaper, the disposable diaper is configured so as to have, for example, a front abdomen part, a rear back part, and a crotch part positioned therebetween and provided with the absorbent body. The front abdomen part is a part applied to an abdomen side of a wearer in wearing the disposable diaper, and the rear back part is a part applied to a back side of the wearer in wearing the disposable diaper. The crotch part is a part positioned between the front abdomen part and the rear back part and applied to a crotch of the wearer.

The disposable diaper may be a tape-type disposable diaper or may be a pants-type disposable diaper. The tape-type disposable diaper is, for example, configured such that fastening members are provided on both end parts in the width direction of a rear back part, and can be formed into a pants shape in wearing by fastening the fastening members to the front abdomen part. The pants-type disposable diaper has a pants shape having a waist opening and a pair of leg openings, and is formed in a pants shape before wearing.

In the case that the absorbent article is a disposable diaper, the disposable diaper is configured such that, for example, a laminate comprising a top sheet, a back sheet and an absorbent body provided therebetween has a front abdomen part, a rear back part and a crotch part positioned therebetween. The disposable diaper may be also configured so as to comprise an exterior member having a front abdomen part, a rear back part and a crotch part positioned therebetween, and an absorbent body comprising a top sheet, a back sheet and an absorbent body provided therebetween, wherein the absorbent body is provided at the crotch part of the exterior member. In the latter case, by forming the exterior member into a pants shape, the pants-type disposable diaper can be obtained. In any case, the absorbent article of the present invention can be obtained by providing a leak-proof flap on the skin facing side of the absorbent article and configuring the leak-proof flap as described above.

This application claims priority to Japanese Patent Application No. 2019-132057, filed on Jul. 17, 2019. All of the contents of the Japanese Patent Application No. 2019-132057, filed on Jul. 17, 2019, are incorporated by reference herein.

REFERENCE SIGNS LIST 1, 1A, 1B, 1C: an absorbent article
2: a top sheet
3: a back sheet
4: an absorbent body
5: a side sheet, 5A: a base part, 5B: a folded part, $5B_1$: a first folded part, $5B_2$: a second folded part
6: a leak-proof flap, 6F: a front end portion, 6B: a rear end portion, 6M: a middle portion
7: a flap elastic member
8: an end fixing part, 8A: a first end fixing part, 8B: a second end fixing part
10: a second flap elastic member

The invention claimed is:
1. An absorbent article comprising a top sheet, a back sheet, an absorbent body provided therebetween, and side sheets provided on both sides of the top sheet in a width direction, wherein:
  a leak-proof flap is formed from a portion of the side sheet;
  the leak-proof flap has a front end portion, a rear end portion and a middle portion positioned therebetween in a longitudinal direction, wherein the front end portion and the rear end portion are joined to the top sheet at end fixing parts, the middle portion stands up inward in the width direction from a joint part where the side sheet is joined to the top sheet, a rear end of the end fixing part provided on the front end portion is a boundary between the front end portion and the middle portion, and a front end of the end fixing part provided on the rear end portion is a boundary between the rear end portion and the middle portion;

a flap elastic member is provided on the leak-proof flap so as to extend continuously from the front end portion to the rear end portion; and the flap elastic member at the front end portion and the rear end portion is located inward in the width direction from the end fixing parts.

2. An absorbent article comprising a top sheet, a back sheet, an absorbent body provided therebetween, and side sheets provided on both sides of the top sheet in a width direction, wherein:

the side sheet has a base part provided facing the top sheet and a folded part formed by folding back the side sheet at an inner edge of the base part in the width direction;

a leak-proof flap is formed from the folded part of the side sheet;

the leak-proof flap has a front end portion, a rear end portion and a middle portion positioned therebetween in a longitudinal direction, wherein the front end portion and the rear end portion are joined to the base part of the side sheet at end fixing parts, the middle portion stands up outward in the width direction from a joint part where the side sheet is joined to the top sheet, a rear end of the end fixing part provided on the front end portion is a boundary between the front end portion and the middle portion, and a front end of the end fixing part is a boundary between the rear end portion and the middle portion;

an outer edge of the folded part in the width direction at the front end portion and the rear end portion is located so as to overlap with the absorbent body in a plan view of the absorbent article;

a flap elastic member is provided on the leak-proof flap so as to extend continuously from the front end portion to the rear end portion; and the flap elastic member at the front end portion and the rear end portion is located outward in the width direction from the end fixing parts.

3. An absorbent article comprising a top sheet, a back sheet, an absorbent body provided therebetween, and side sheets provided on both sides of the top sheet in a width direction, wherein:

the side sheet has a base part provided facing the top sheet, a first folded part formed by folding back the side sheet at an inner edge of the base part in the width direction, and a second folded part formed by folding back the side sheet at an outer edge of the first folded part in the width direction;

the leak-proof flap is formed from the first folded part and the second folded part of the side sheet;

the leak-proof flap has a front end portion, a rear end portion and a middle portion positioned therebetween in a longitudinal direction, wherein the front end portion and the rear end portion of the first folded part are joined to the base part of the side sheet at first end fixing parts, the front end portion and the rear end portion of the second folded part are joined to the first folded part of the side sheet at second end fixing parts, the middle portion of the first folded part stands up outward in the width direction from a joint part where the side sheet is joined to the top sheet, a rear end of the first end fixing part provided on the front end portion is a boundary between the front end portion and the middle portion, and a front end of the first end fixing part provided on the rear end portion is a boundary between the rear end portion and the middle portion;

the flap elastic member is provided at the first folded part and/or the second folded part so as to extend continuously from the front end portion to the rear end portion; and the flap elastic member at the front end portion and the rear end portion is located outward in the width direction from the first end fixing parts.

4. The absorbent article according to claim 3, wherein a second flap elastic member is provided at the middle portion of the second folded part, inward in the width direction from an outer end of the first end fixing part in the width direction.

5. The absorbent article according to claim 1, wherein a plurality of the flap elastic members are provided on the leak-proof flap, inward in the width direction from the end fixing part.

6. The absorbent article according to claim 2, wherein a plurality of the flap elastic members are provided on the leak-proof flap, outward in the width direction from the end fixing part.

7. The absorbent article according to claim 1, wherein the flap elastic member is attached to the leak-proof flap with an adhesive applied to the flap elastic member.

8. The absorbent article according to claim 2, wherein the flap elastic member is attached to the leak-proof flap with an adhesive applied to the flap elastic member.

9. The absorbent article according to claim 3, wherein a plurality of the flap elastic members are provided on the leak-proof flap, outward in the width direction from the first end fixing part.

10. The absorbent article according to claim 3, wherein the flap elastic member is attached to the leak-proof flap with an adhesive applied to the flap elastic member.

11. The absorbent article according to claim 3, wherein an outer edge of the first folded part in the width direction at the front end portion and the rear end portion is located so as to overlap with the absorbent body in a plan view of the absorbent article.

* * * * *